(12) United States Patent
Pfotenhauer et al.

(10) Patent No.: US 12,207,806 B2
(45) Date of Patent: Jan. 28, 2025

(54) SURGICAL TOOL ATTACHMENT DEVICES, SYSTEMS, AND METHODS

(71) Applicant: Pro-Dex, Inc., Irvine, CA (US)

(72) Inventors: Alexander M. Pfotenhauer, Tustin, CA (US); Cesar Morales, Irvine, CA (US); Jake Huntley, Yorba Linda, CA (US)

(73) Assignee: PRO-DEX, INC., Irvine, CA (US)

( * ) Notice: Subject to any disclaimer, the term of this patent is extended or adjusted under 35 U.S.C. 154(b) by 582 days.

(21) Appl. No.: 17/374,326

(22) Filed: Jul. 13, 2021

(65) Prior Publication Data

US 2021/0401415 A1 Dec. 30, 2021

Related U.S. Application Data

(63) Continuation of application No. 16/547,386, filed on Aug. 21, 2019, now Pat. No. 11,076,842.

(Continued)

(51) Int. Cl.
*A61B 17/00* (2006.01)

(52) U.S. Cl.
CPC .... *A61B 17/00* (2013.01); *A61B 2017/00438* (2013.01); *A61B 2017/0046* (2013.01);
(Continued)

(58) Field of Classification Search
CPC ......... A61B 17/00; A61B 17/14; A61B 17/16; A61B 17/1617; A61B 17/162;
(Continued)

(56) References Cited

U.S. PATENT DOCUMENTS

| 3,302,328 A | 2/1967 | King |
| 3,992,797 A | 11/1976 | Kazakevich |

(Continued)

FOREIGN PATENT DOCUMENTS

| CN | 2892711 Y | * | 4/2007 |
| CN | 102333490 A | | 1/2012 |

(Continued)

OTHER PUBLICATIONS

International Search Report and Written Opinion in corresponding International Patent Application No. PCT/US2019/047531, dated Oct. 31, 2019, in 9 pages.

(Continued)

*Primary Examiner* — Tammie K Marlen
*Assistant Examiner* — Maria Catherine Anthony
(74) *Attorney, Agent, or Firm* — Knobbe, Martens, Olson & Bear, LLP

(57) ABSTRACT

A locking adapter configured to removably attach a surgical tool to a surgical handpiece unit can include a first coupling portion having a first hole and a second coupling portion having a second hole. The first and second holes can receive a portion of a surgical instrument, such as a cutting element (e.g., a burr or blade). The locking adapter can have a first position where the first hole is not aligned with the second hole and a second position where the first hole is aligned with the second hole. When the locking adapter is in the second position and the portion of the surgical instrument is received within the first and second holes, the first coupling portion can apply a first force on the portion and the second coupling portion can apply a second force on the portion, the first and second forces having different directions.

18 Claims, 11 Drawing Sheets

Related U.S. Application Data

(60) Provisional application No. 62/726,022, filed on Aug. 31, 2018.

(52) U.S. Cl.
CPC ............... *A61B 2017/00486* (2013.01); *A61B 2017/00862* (2013.01)

(58) Field of Classification Search
CPC ............... A61B 17/1622; A61B 17/32; A61B 2017/00296; A61B 2017/00424; A61B 2017/00438; A61B 2017/0046; A61B 2017/00473; A61B 2017/00477; A61B 2017/00486; A61B 2017/00862
USPC ............................................................ 606/1
See application file for complete search history.

(56) References Cited

U.S. PATENT DOCUMENTS

| | | | |
|---|---|---|---|
| D400,298 S | 10/1998 | Vignerot | |
| 6,122,806 A | 9/2000 | Umezawa et al. | |
| 6,235,001 B1 * | 5/2001 | O'Holloran | A61M 37/0069 604/165.02 |
| 6,261,303 B1 | 7/2001 | Mayenberger et al. | |
| 6,524,306 B1 | 2/2003 | Hennig | |
| 6,722,047 B2 | 4/2004 | Baber et al. | |
| 8,070,690 B2 | 12/2011 | Ikehara et al. | |
| 9,211,373 B2 | 12/2015 | Dexter et al. | |
| 10,219,810 B2 | 3/2019 | Mimran | |
| 11,076,842 B2 | 8/2021 | Pfotenhauer et al. | |
| 2002/0022800 A1 | 2/2002 | O'Holloran et al. | |
| 2007/0266529 A1 | 11/2007 | Paul | |
| 2012/0041260 A1 | 2/2012 | Yamada | |
| 2013/0079751 A1 | 3/2013 | Dexter et al. | |
| 2014/0290032 A1 | 10/2014 | Kleven | |
| 2016/0000449 A1 | 1/2016 | Aman et al. | |
| 2017/0000496 A1 | 1/2017 | Hershberger | |
| 2017/0333077 A1 | 11/2017 | Williams et al. | |
| 2018/0035987 A1 | 2/2018 | Williams et al. | |
| 2018/0064503 A1 | 3/2018 | Young | |

FOREIGN PATENT DOCUMENTS

| | | |
|---|---|---|
| CN | 103958792 A | 7/2014 |
| CN | 107773296 A | 3/2018 |
| CN | 207462143 U | 6/2018 |
| GB | 2337291 A | 11/1999 |
| JP | H0930493 A | 2/1997 |
| WO | WO 2017/046531 A1 | 3/2017 |

OTHER PUBLICATIONS

European Search Report received in Application No. 19853318.4 dated Apr. 19, 2022, in 12 pages.
International Preliminary Report on Patentability in corresponding International Patent Application No. PCT/US2019/047531, dated Mar. 11, 2021, in 6 pages.
Surgical Tool Attachment Devices, Systems, and Methods, U.S. Appl. No. 16/547,386, U.S. Pat. No. 11,076,842.

* cited by examiner

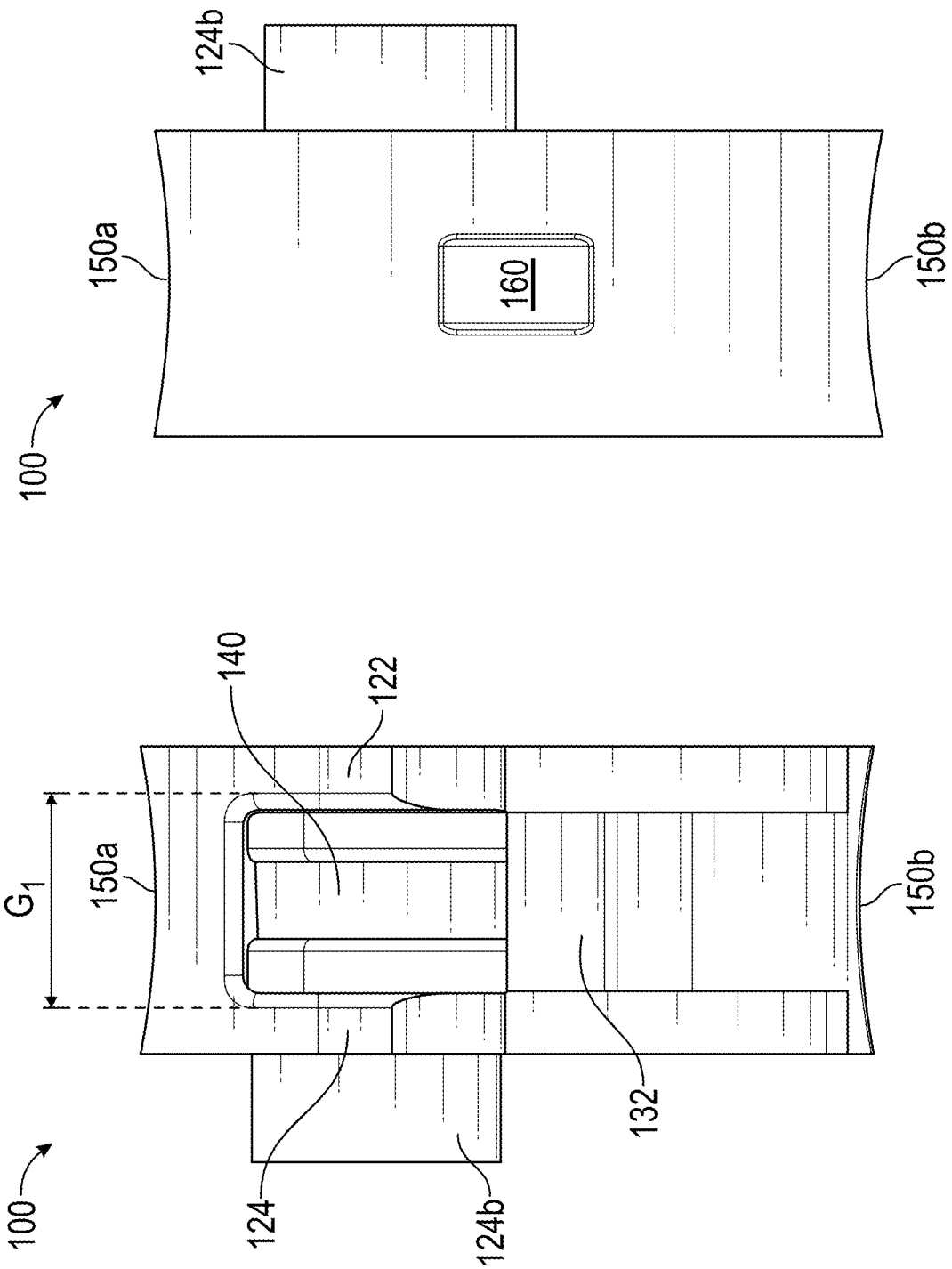

SURGICAL TOOL ATTACHMENT DEVICES, SYSTEMS, AND METHODS

CROSS REFERENCE

This application is a continuation of U.S. patent application Ser. No. 16/547,386, filed Aug. 21, 2019, which claims the benefit of U.S. Patent Application No. 62/726,022, filed Aug. 31, 2018, the entirety of each of which is incorporated by reference herein.

BACKGROUND

Field

This disclosure generally relates to devices, systems, and methods for attaching tools to a surgical instrument, such as a cutting element, that is operably connected with a surgical handpiece.

Certain Related Art

In certain surgical procedures, such as arthroscopic surgical procedures, a surgical instrument is driven by a surgical handpiece. The surgical instrument can be a cutting element, such as a burr or blade. The surgical instrument can be an elongate member with a proximal end received in the handpiece and a distal end with a cutting head, such as a blade. A motor in the handpiece can rotate the surgical instrument, such as to provide cutting functionality to remove tissue during a surgical procedure.

SUMMARY OF CERTAIN FEATURES

It could be beneficial to be able to securely and removably couple a separate tool to the surgical instrument. This could, for example, provide different functionality (e.g., functionality other than the specific cutting purpose of a cutting element) without the need to remove and replace the surgical instrument, which can be inconvenient and time consuming. For example, it could be beneficial to be able to quickly and easily couple a mirror, sensor, or other tool to the surgical instrument while maintaining the surgical instrument in the handpiece, and then to quickly and easily remove the mirror, sensor, or other tool from the surgical instrument while maintaining the surgical instrument in the handpiece. It could be beneficial to be able to couple the tool to the surgical instrument without requiring a modification to, or a special version of, the surgical instrument and/or without damaging the surgical instrument. Moreover, it could be beneficial to be able to vary the position of the tool along the length of the surgical instrument and/or to have a distal end of the tool extend beyond a distal end of the surgical instrument.

This disclosure relates to devices, systems, and methods that address one or more of the above concerns, or other concerns. This disclosure describes various devices, systems, and methods that allow a user, such as a surgeon or other medical professional, to attach a tool to a surgical instrument that is mounted in a surgical handpiece. The tool can be coupled to the surgical instrument at a point of use, such as in an operating room. The tool can be contained in sterilized packaging and disposed of after use. The tool can be removed from the sterilized packaging at the point of use for surgical procedures.

A locking adapter configured to removably attach a surgical tool to a surgical handpiece unit can comprise: a first leg having a first end and a second end opposite the first end; a second leg having a third end and a fourth end opposite the third end, wherein the third end of the second leg is connected to the second end of the first leg; a first coupling portion connected to the first end of the first leg and comprising a first hole; and a second coupling portion connected to the fourth end of the second leg and comprising a second hole, wherein the first and second holes are configured to receive a portion of a surgical instrument of the surgical handpiece unit. In some embodiments, the locking adapter has a first position where the first hole of the first coupling portion is not aligned with the second hole of the second coupling portion and a second position where the first hole is aligned with the second hole, and, when the locking adapter is in the second position and the portion of the surgical instrument is received within the first and second holes, the first coupling portion applies a first force on the portion and the second coupling portion applies a second force on the portion, the first and second forces having different directions. In some embodiments, the first coupling portion extends from the first end of the first leg in a direction that is non-parallel to a length of the first leg and the second coupling portion extends from the fourth end of the second leg in a direction that is non-parallel to a length of the second leg. In some embodiments, the first coupling portion extends from the first end of first leg toward the second coupling portion and the second coupling portion extends from the fourth end of second leg toward the first coupling portion.

In some embodiments, the first coupling portion comprises a first foot and a second foot and each of the first and second feet extend from the first end of the first leg, wherein the first foot comprises the first hole and the second foot comprises a third hole. In some embodiments, the first and second feet are spaced apart from one another by a gap, the gap configured to accommodate the second coupling portion when the locking adapter is in the second position. In some embodiments, the first hole, second hole, and third hole comprise a circular cross-section. In some embodiments, the second hole and at least one of the first and third hole comprise cross-sections having equal cross-sectional area. In some embodiments, when the locking adapter is in the second position, axes extending through centers of the first, second, and third holes align with each other. In some embodiments, when the locking adapter is in the first and second positions, the first and third holes of the first coupling portion align.

In some embodiments, when the locking adapter is in the first position, a first axis extending through the first hole is parallel with a second axis extending through the second hole. In some embodiments, when the locking adapter is in the second position, the first axis extending through the first hole is aligned with the second axis extending through the second hole.

In some embodiments, the locking adapter further comprises a first recessed portion located on the first end of the first leg, the first recessed portion configured to at least partially conform to a shape of a first finger of a user. In some embodiments, the locking adapter further comprises a second recessed portion located on the fourth end of the second leg, the second recessed portion configured to at least partially conform to a shape of a second finger of the user. In some embodiments, the first recessed portion and the second recessed portion are aligned.

In some embodiments, the first leg, second leg, first coupling portion, and second coupling portion define an opening extending through an interior area of the locking adapter. In some embodiments, when the locking adapter is in the first position, the opening comprises a rounded triangle shape.

In some embodiments, when the locking adapter is in the first position, the locking adapter comprises a triangular shape. In some embodiments, the first leg is integral with the second leg. In some embodiments, the first coupling portion is integral with the first leg. In some embodiments, the second coupling portion is integral with the second leg.

In some embodiments, the first and second legs have interior surfaces facing at least partially toward the first and second coupling portions and exterior surfaces opposite the interior surfaces. In some embodiments, the locking adapter further comprises a rib extending outward from and along a portion of the interior surfaces of the first and second legs. In some embodiments, the locking adapter further comprises a first recessed portion positioned on the exterior surface of the first leg proximate the first end. In some embodiments, the locking adapter further comprises a second recessed portion positioned on the exterior surface of the second leg proximate the fourth end. In some embodiments, the first recessed portion and the second recessed portion are aligned. In some embodiments, at least one of the first recessed portion and the second recessed portion is sized and shaped to conform to a thumb of the user.

In some embodiments, the locking adapter further comprises a tool-engagement portion configured to secure an end of the surgical tool. In some embodiments, the tool-engagement portion extends outward from the first coupling portion and around the first hole. In some embodiments, the tool-engagement portion is configured to receive the end of the surgical tool. In some embodiments, the tool-engagement portion is configured to receive a portion of a bushing, the bushing comprising a through-hole sized and shaped to receive the end of the surgical tool. In some embodiments, the tool-engagement portion comprises a cylindrical cross-section. In some embodiments, the first coupling portion applies the first force at a first location along a length of the surgical instrument and the second coupling portion applies the second force along a second location along the length of the surgical instrument, and wherein the first location is spaced from the second location by a distance.

A method of securing a surgical tool to a surgical instrument, the surgical tool comprising a shaft having a first end and a second end opposite the first end, the surgical instrument configured to secure to a surgical handpiece, can comprise: obtaining a locking adapter, the locking adapter comprising: a first leg having a first end and a second end opposite the first end; a second leg having a third end and a fourth end opposite the third end, wherein the third end of the second leg is connected to the second end of the first leg; a first coupling portion connected to the first end of the first leg and comprising a first hole; and a second coupling portion connected to the fourth end of the second leg and comprising a second hole; aligning the first hole of the first coupling portion with the second hole of the second coupling portion; positioning a first portion of the surgical instrument within the first and second holes of the first and second coupling portions of the locking adapter; releasing the locking adapter thereby securing the locking adapter to the portion of the surgical instrument due to a physical engagement between the locking adapter and the surgical instrument; and securing the second end of the surgical tool to the first coupling portion.

In some embodiments, the locking adapter further comprises a tool-engagement portion extending outward from the first coupling portion and around the first hole, and wherein the method further comprises securing the second end of the surgical tool within the tool-engagement portion.

In some embodiments, the method further comprises positioning a bushing at least partially within the tool-engagement portion of the first coupling portion, the bushing comprising a through-hole sized and shaped to receive the second end of the surgical tool. In some embodiments, the surgical tool comprises a shaft and at least one collar, and wherein the method further comprises at least partially securing the surgical tool to the surgical instrument by positioning the at least one collar around a second portion of the surgical instrument. In some embodiments, the positioning of the at least one collar around the second portion of the surgical instrument occurs prior to the positioning of the first portion of the surgical instrument within the first and second holes of the first and second coupling portions of the locking adapter.

In some embodiments, said aligning the first hole of the first coupling portion with the second hole of the second coupling portion comprises applying at least one force to the locking adapter. In some embodiments, said at least one force comprises a first force proximate to the first end of the first leg and a second force proximate to the fourth end of the second leg. In some embodiments, said first force is applied in a first direction and said second force is applied in a second direction opposite the first direction. In some embodiments, said first force is applied at a first recessed portion of the first leg and said second force is applied at a second recessed portion of the second leg.

In some embodiments, when the locking adapter is released, the first coupling applies a first force at a first location along a length of the surgical instrument and the second coupling portion applies a second force at a second location along the length of the surgical instrument, the first and second forces having different directions. In some embodiments, the first and second forces have opposite directions. In some embodiments, the first location and the second location are spaced apart from one another by a distance. In some embodiments, the first coupling portion comprises a first foot and a second foot, each of the first and second feet extending from the first end of the first leg, and wherein the first foot comprises the first hole and the second foot comprises a third hole.

In some embodiments, when the locking adapter is released: the first foot of the first coupling portion applies a first force at a first location along a length of the surgical instrument; the second foot of the first coupling portion applies a second force at a second location along the length of the surgical instrument; and the second coupling portion applies a third force at a third location along the length of the surgical instrument, wherein the third force is applied in a direction opposite that of the first and second forces. In some embodiments, the first and second feet of the first coupling portion are spaced apart from one another by a gap, the gap configured to accommodate the second coupling portion when the locking adapter is in the second position.

A locking adapter configured to removably attach a surgical tool to a surgical handpiece unit can comprise: a first leg, the first leg comprising a free end with a first receiving region; a second leg, the second leg comprising a free end with a second receiving region; a biased apex that connects the first leg and the second leg such that the first leg and the second leg are resiliently movable relative to each other; and a tool engaging region configured to receive a surgical tool. The locking adapter can be configured such that: in response to a force being applied against the bias of the apex to the first and second legs, the locking adapter transitions from a rest state in which the first and second receiving regions are misaligned to an energized state in which the first and second receiving regions are aligned, thereby permitting the surgical instrument to be longitudinally inserted into the first and second receiving regions; and in response to the force being removed from the first and second legs, the adapter automatically pinches the surgical instrument between the first leg and the second leg, thereby securely coupling the locking adapter to the surgical instrument. In some embodiments, the tool engaging region extends around the first receiving region of the first leg. In some embodiments, the locking adapter further comprises a first recessed portion positioned at the free end of the first leg, the first recessed portion configured to at least partially conform to a shape of a first finger of a user. In some embodiments, the locking adapter further comprises a second recessed portion positioned at the free end of the second leg, the second recessed portion configured to at least partially conform to a shape of a second finger of the user, wherein the first and second recessed portions are aligned. In some embodiments, the first and second receiving regions comprise a circular cross-section.

Any of the structures, materials, steps, or other features disclosed above, or disclosed elsewhere herein, can be used in any of the embodiments in this disclosure. Any structure, material, step, or other feature of any embodiment can be combined with any structure, material, step, or other feature of any other embodiment to form further embodiments, which are part of this disclosure.

The preceding summary is meant to be a high-level summary of certain features within the scope of this disclosure. The summary, the following detailed description, and the associated drawings do not limit or define the scope of protection. The scope of protection is defined by the claims. No feature is critical or indispensable.

BRIEF DESCRIPTION OF THE DRAWINGS

Certain features of this disclosure are described below with reference to the drawings. The illustrated embodiments are intended to illustrate, but not to limit the embodiments. Various features of the different disclosed embodiments can be combined to form further embodiments, which are part of this disclosure.

FIG. 2J illustrates a front view of the locking adapter of FIG. 1A.

FIG. 2K illustrates a back view of the locking adapter of FIG. 1A.

DETAILED DESCRIPTION OF CERTAIN EMBODIMENTS

Various features and advantages of the disclosed technology will become more fully apparent from the following description of the several specific embodiments illustrated in the figures. These embodiments are intended to illustrate the principles of this disclosure. However, this disclosure should not be limited to only the illustrated embodiments. The features of the illustrated embodiments can be modified, combined, removed, and/or substituted as will be apparent to those of ordinary skill in the art upon consideration of the principles disclosed herein.

Overview

Figure 1A:
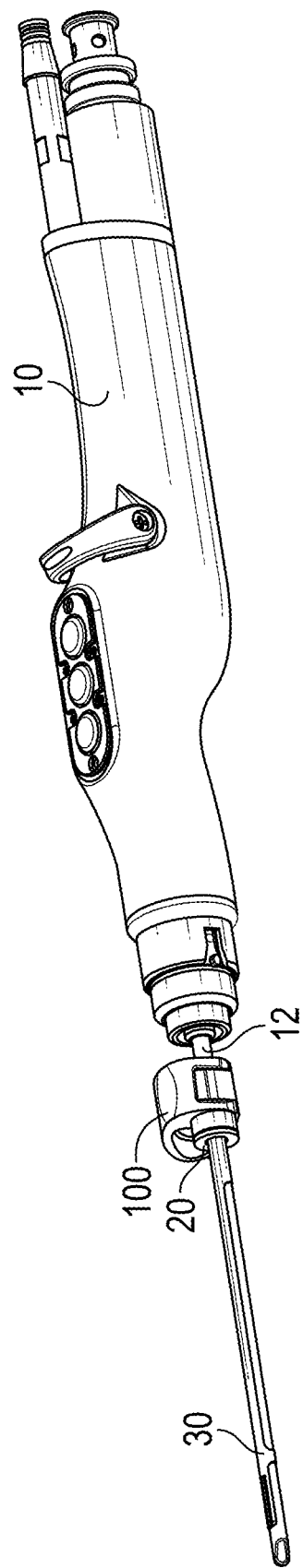
FIG. 1A illustrates a handpiece, a surgical instrument secured to the handpiece, a tool partially secured around the surgical instrument, and a locking adapter and bushing for attaching the tool to the surgical instrument in accordance with aspects of this disclosure.

FIG. 1A illustrates a surgical instrument 12 attached to a surgical handpiece 10. The surgical instrument 12 can be attached to a drive head of the surgical handpiece 10 at an end of the surgical instrument 12, for example. The surgical instrument 12 can be any instrument that can secure, attach, and/or couple with a portion of the surgical handpiece 10 in order to perform an operation useful for a surgical operation. For example, the surgical instrument 12 can be a surgical burr or blade. The surgical handpiece 10 (also referred to herein as "handpiece") can be any medical device capable of securing a surgical instrument 12 and performing surgical procedures or operations (such as an arthroscopic shaver) with the surgical instrument 12. For example, the surgical handpiece 10 can be the same in some, many, or all respects as the handheld medical device described in U.S. Pat. No. 8,747,392, which is incorporated herein in its entirety.

FIG. 1A further illustrates a surgical tool 30 (also referred to herein as a "surgical attachment") at least partially secured to and/or around the surgical instrument 12. As shown, a portion (e.g., an end) of the surgical tool 30 can be secured by a locking adapter 100, which is discussed in more detail below. As also shown, the locking adapter 100 can secure (and/or secure to) a portion of the surgical tool 30 and can also secure (and/or secure to) a portion of the surgical instrument 12. As shown, the surgical tool 30 and surgical instrument 12 can be generally parallel and/or co-axial. In order to accommodate different sizes and/or shapes of the surgical tool 30 (or an end thereof), a bushing 20 can be positioned in the locking adapter 100. The bushing 20 can receive and secure the surgical tool 30, as described in more detail below.

Figure 1B:
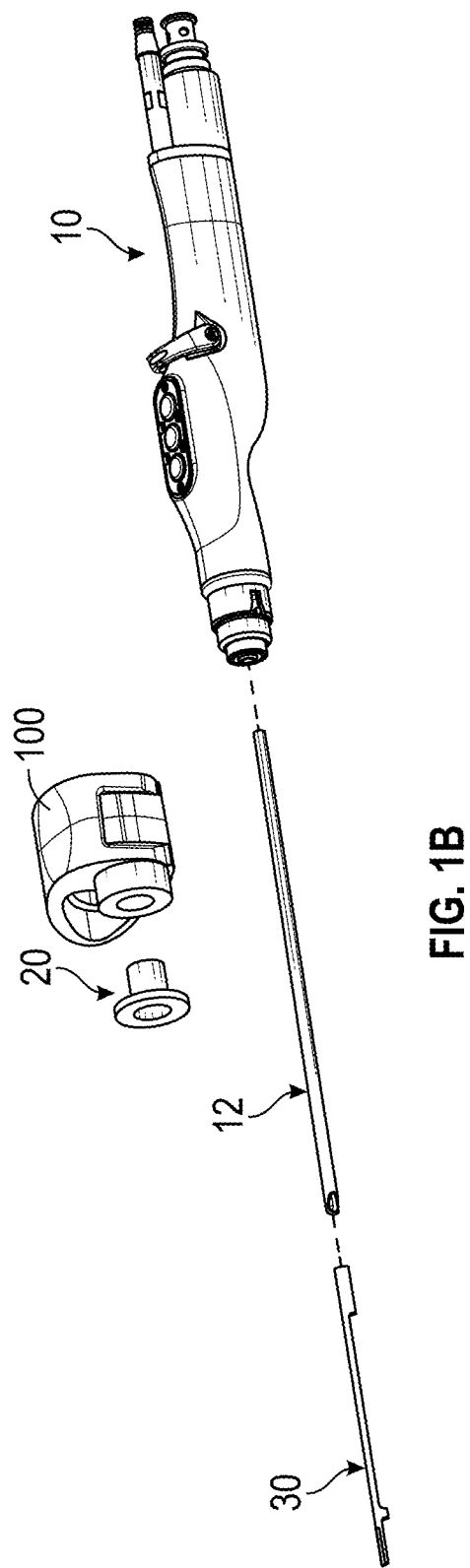
FIG. 1B illustrates an exploded view of the handpiece, surgical instrument, tool, and locking adapter and bushing of FIG. 1A.

FIG. 1B illustrates an exploded view of the handpiece 10, surgical instrument 12, locking adapter 100, bushing 20, and surgical tool 30. As described in more detail below, the surgical tool 30 can be attached to surgical instrument 12 indirectly via the locking adapter 100 and/or directly via one or more features of the surgical tool 30 (for example, one or more collars which can be sized and/or shaped to receive portions of the surgical instrument 12).

Locking Adapter

FIGS. 2A-2K illustrate various views of the locking adapter 100. As discussed herein, the locking adapter 100 can be used to secure a surgical tool 30 to a surgical instrument 12 (for example, a burr). Advantageously, the locking adapter 100 can facilitate attachment of the surgical tool 30 to the surgical instrument 12 at or before a point of use in an operating environment. The locking adapter 100 can include a tool-engagement portion (such as the tool-engagement portion 124b described further below) for securing a portion of the surgical tool 30 and a surgical instrument-engagement portion, such as one or more coupling portions 120, 130 described further below. The locking adapter 100 can secure to a portion of surgical tool 30 before, during, or after securing to one or more portions of the surgical instrument 12.

As shown in at least FIGS. 2A-2H, the locking adapter 100 can include a first leg 110 and a second leg 112. The legs 110, 112 can be connected at ends thereof, such as at a corner or an apex of the adapter 100 as illustrated. The first and second legs 110, 112 can be resiliently connected and/or can be biased, such as toward the position shown in FIG. 2A. The first leg 110 can have a first end and a second end opposite the first end. The second leg 112 can also include a first end and a second end opposite the first end. The first end of the first leg 110 can be free and the second end of the first leg 110 can be connected to an end of the second leg 112 (such as the first end of the second leg 112). The second end of the second leg 112 can be free. Thus, the first and second legs 110, 112 can each have a free end (e.g., an end not connected to anything else) and a connected end. In some embodiments, the first and second legs 110, 112 are integral (e.g., unitarily formed as one piece).

As discussed above, the locking adapter 100 can include a surgical instrument-engagement portion, which can secure to one or more portions of the surgical instrument 12. For example, the locking adapter 100 can include a first coupling portion 120. The first coupling portion 120 can be connected with an end of the first leg 110. For example, the first coupling portion 120 can be located on the first (free) end of first leg 110. In some embodiments, the first coupling portion 120 is integral with the first leg 110. In some embodiments, the first coupling portion 120 extends from the first leg 110 in a direction that is non-parallel to a length of the first leg 110. For example, the first leg 110 can have a length extending between the first end and the second end thereof, and the first coupling portion 120 can extend from the first leg 110 (and/or the first end of the first leg 110) at an angle that is equal to 10 degrees, 20 degrees, 30 degrees, 40 degrees, 50 degrees, 60 degrees, 70 degrees, 80 degrees, 90 degrees, 100 degrees, 110 degrees, 120 degrees, 130 degrees, 140 degrees, 150 degrees, 160 degrees, or 170 degrees with respect to the length of the first leg 110, or any value therebetween, or any range bounded by any combination of these values, although other values outside these ranges are possible. In some embodiments, the first coupling portion 120 extends toward an end of the second leg 112 and/or a second coupling portion 130 of the second leg 112 which are described further below.

In some embodiments, the first coupling portion 120 defines the first (free) end of the first leg 110. For example, the first leg 110 of the locking adapter 100 can have a second end which connects to the second leg 112 and a first end, opposite the second end, which is defined by the first coupling portion 120. In such cases, the first coupling portion 120 can curl and/or extend in a direction that is non-parallel with respect to a portion of a length of the first leg 110 between the second end (connected to the second leg 112) and the first end of the first leg 110.

The first coupling portion 120 can include one or more openings which are sized and/or shaped to receive a portion of the surgical instrument 12. When a portion of the surgical instrument 12 is positioned and/or secured within such one or more openings of the first coupling portion 120, the first coupling portion 120 can secure the locking adapter 100 to the portion of the surgical instrument 12. Further, when the first coupling portion 120 secures to the portion of the surgical instrument 12 in such manner, another portion of the locking adapter 100 (such as the tool-engagement portion 124b) can secure to a portion of a surgical tool 30 so as to attach the surgical tool 30 to the surgical instrument 12. Such one or more openings of the first coupling portion 120 can be, for example, through-holes.

Figure 2A:
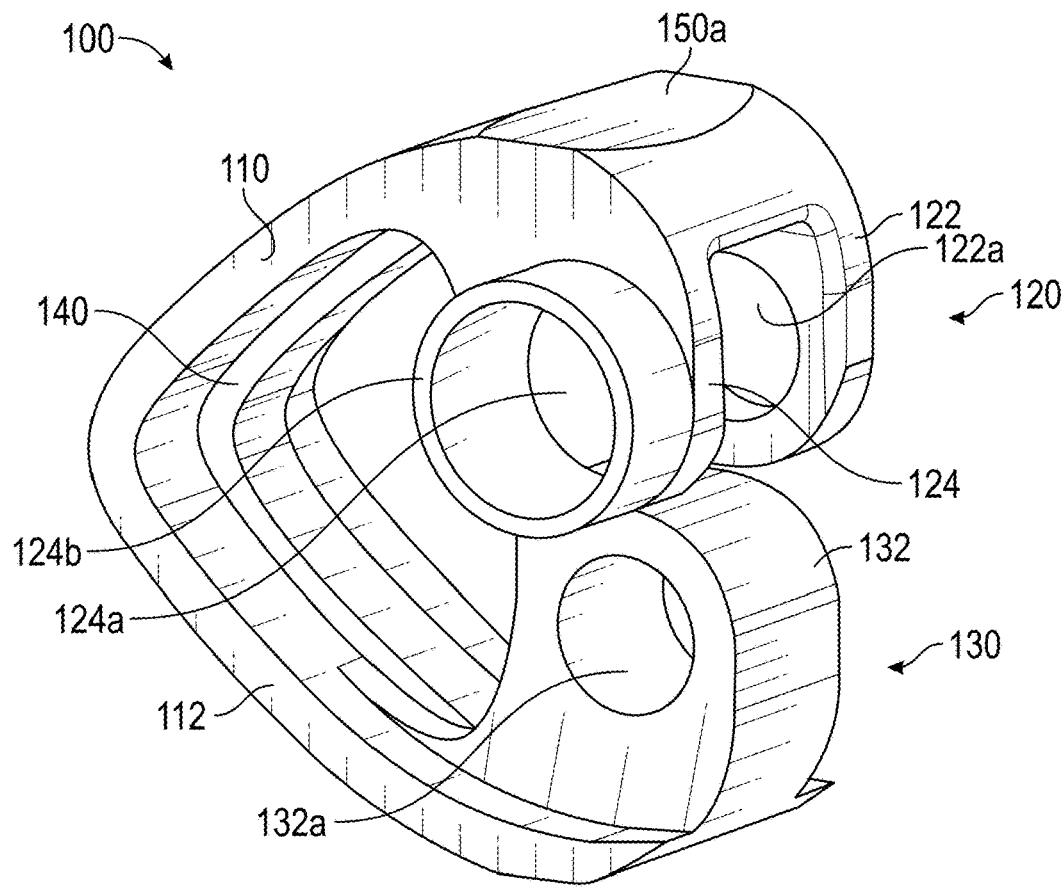
FIG. 2A illustrates a perspective view of the locking adapter of FIG. 1A in accordance with aspects of this disclosure.
Figure 2B:
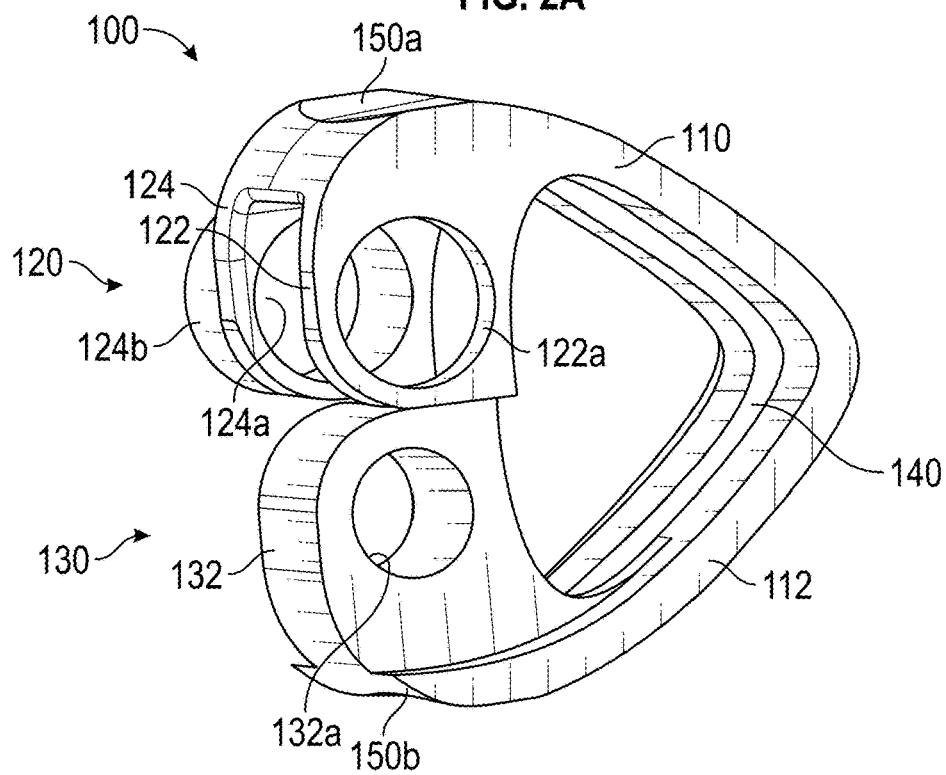
FIG. 2B illustrates another perspective view of the locking adapter of FIG. 1A.
Figure 2C:
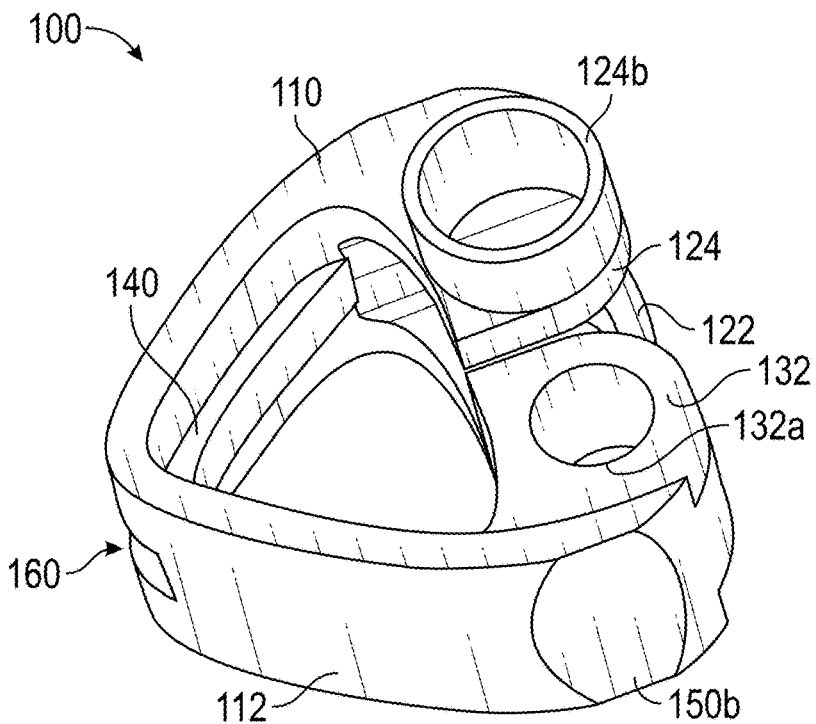
FIG. 2C illustrates another perspective view of the locking adapter of FIG. 1A.
Figure 2D:
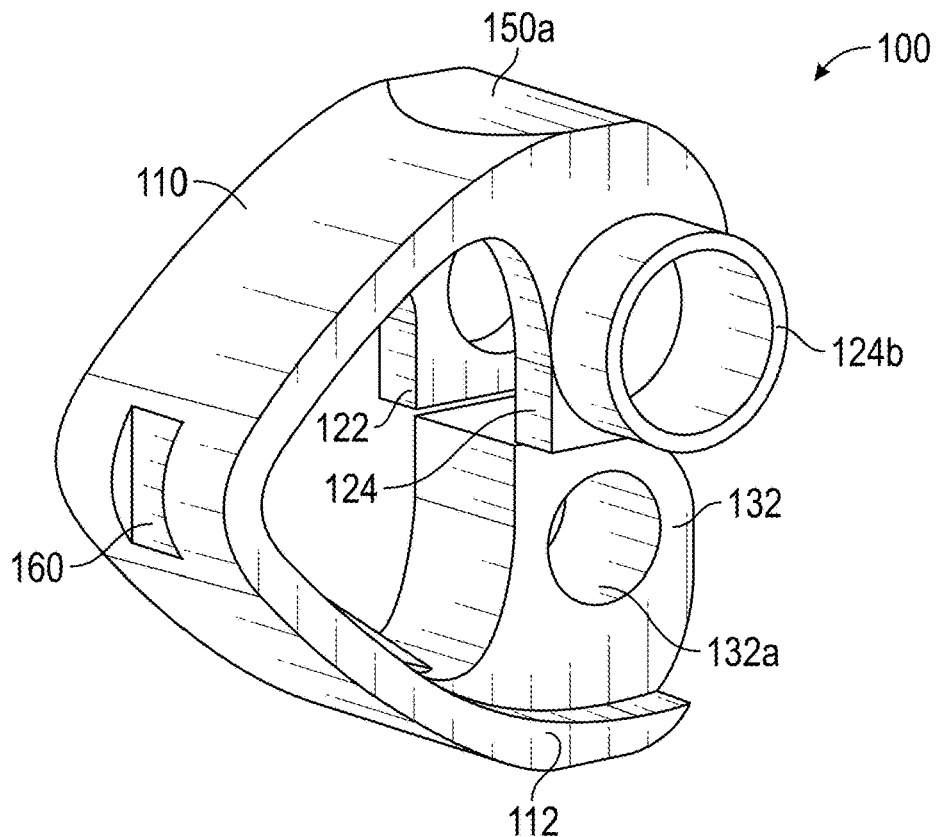
FIG. 2D illustrates another perspective view of the locking adapter of FIG. 1A.
Figure 2E:
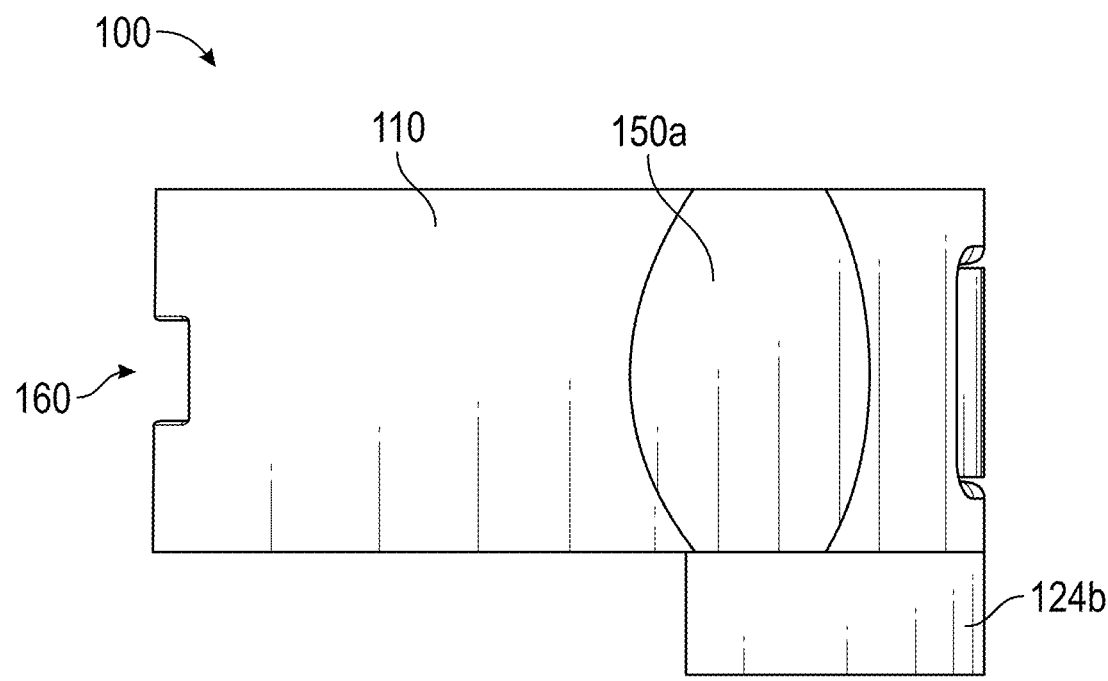
FIG. 2E illustrates a top view of the locking adapter of FIG. 1A.
Figure 2F:
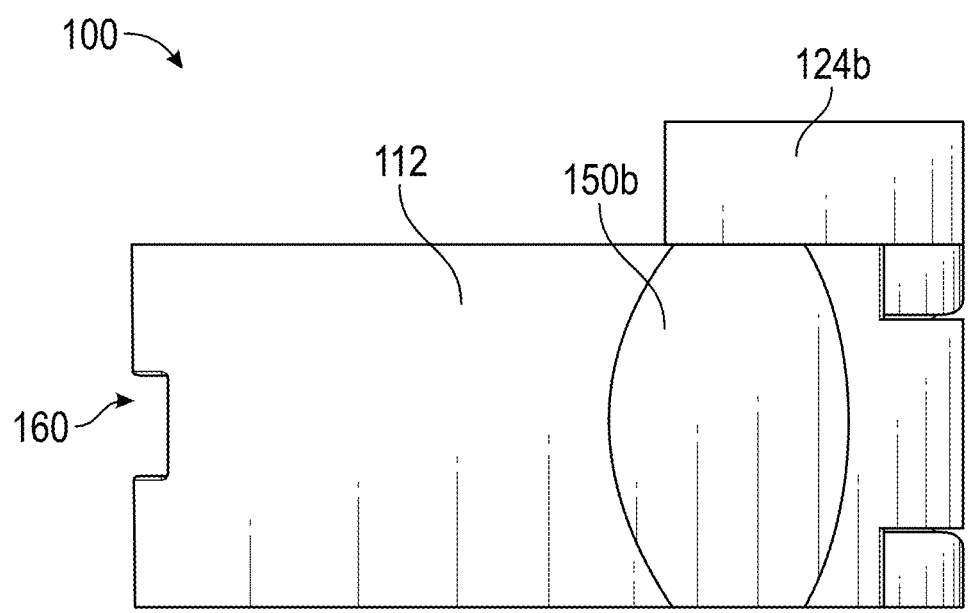
FIG. 2F illustrates a bottom view of the locking adapter of FIG. 1A.

As shown in at least FIGS. 2A-2B, the first coupling portion 120 can comprise a first foot 122 which can at least partially receive, secure to, and/or engage a portion of the surgical instrument 12. For example, the first foot 122 can include an opening 122a that can be sized and/or shaped to receive a portion of the surgical instrument 12. For example, the opening 122a can be sized and/or shaped to accommodate and/or surround a cross-section (or a portion of a cross-section) of the surgical instrument 12. The opening 122a can have a cross-section that is circular, square, rectangular, pentagonal, hexagonal, heptagonal, octagonal, nonagonal, or decagonal, for example. The opening 122a can be a through-hole.

In some embodiments, the first coupling portion 120 includes a second foot 124. For example, as shown in at least FIGS. 2A-2B, the first coupling portion 120 can include a second foot 124 that is proximate, adjacent, and/or spaced apart from first foot 122. The second foot 124 can at least partially receive, secure to, and/or engage a portion of the surgical instrument 12. The second foot 124 can include an opening 124a that can be sized and/or shaped to receive a portion of the surgical instrument 12. The opening 124a can be sized and/or shaped to accommodate and/or surround a cross-section (or a portion of a cross-section) of the surgical instrument 12. The opening 124a can have a cross-section that is circular, square, rectangular, pentagonal, hexagonal, heptagonal, octagonal, nonagonal, or decagonal, for example. The opening 124a can be a through-hole. The opening 124a can axially align with the opening 122a. In some embodiments, the opening 124a is larger than the opening 122a. For example, with reference to FIG. 2G, the opening 124a can have a larger cross-sectional area than the opening 122a. As another example, in some embodiments, the opening 124a has a circular cross-section with a larger diameter than a circular cross-section of the opening 122a. In some cases, the opening 124a is larger than the opening 122a to accommodate the bushing 20 within the tool-engagement portion 124b.

As discussed above, the locking adapter 100 can include a tool-engagement portion (also referred to herein as "tool engaging region") for securing (and/or securing to) a portion of the surgical tool 30 (such as an end of the surgical tool 30). Such tool-engagement portion can act alongside a surgical instrument-engagement portion (such as the one or more coupling portions 120, 130 described herein) to attach the surgical tool 30 to the surgical instrument 12. Such tool-engagement portion can extend from and/or be connected to a portion of the locking adapter 100, such as the first leg 110, the first end of the first leg 110, the first coupling portion 120, and/or the first or second feet 122, 124. For example, as shown in at least FIGS. 2A-2G, the locking adapter 100 can include a tool-engagement portion 124*b* which extends outward from the second foot 124 of the first coupling portion 110. However, because the locking adapter 100 can include either or both of the first and second feet 122, 124, the tool-engagement portion 124*b* can extend from either of the first and second feet 122, 124, depending on the configuration of the first coupling portion 120. The tool-engagement portion 124*b* can extend outward from a surface the first coupling portion 120 (such as a surface of the second foot 124) at an angle. For example, the tool-engagement portion 124*b* can extend perpendicular (or generally perpendicular) from a surface of the second foot 124. In some embodiments, the tool-engagement portion 124*b* extends outward from a surface of the second foot 124 and extends around a portion of a perimeter of the opening 124*a* of the second foot 124. In some embodiments, the tool-engagement portion 124*b* is a skirt wall extending outward from a surface of the second foot 124 and/or around the perimeter of the opening 124*a*. A length of extension of the tool-engagement portion 124*b* can be modified so as to receive a longer or shorter portion of an end of the surgical tool 30.

The tool-engagement portion 124*b* can have a cylindrical shape with a hollow interior. Alternatively, the tool-engagement portion 124*b* can have a different shape having a hollow interior, for example, a shape that is square, rectangular, pentagonal, hexagonal, heptagonal, octagonal, nonagonal, or decagonal that has a hollow interior therein. The hollow interior of the tool-engagement portion 124*b* can align with the opening 124*a* of the second foot 124 and/or the opening 122*a* of the first foot 122*a*. For example, an axis extending through a center of the hollow interior of the tool-engagement portion 124*b* can align with an axis extending through a center of the opening 124*a* and/or an axis extending through the opening 122*a*. The axes running through the hollow interior, the opening 124*a*, and/or 124*a* can be parallel.

The tool-engagement portion 124*b* can receive and/or secure to a bushing 20 (see FIGS. 1A-1B). The bushing 20 can be sized and/or shaped to be positioned within and/or secured to the tool-engagement portion 124*b*. The bushing 20 can additionally be configured to secure to a portion of the surgical tool 30. The bushing 20 can thus be positioned between a portion of a surgical tool 30 (such as an end of the surgical tool 30) and the tool-engagement portion 124*b* of the locking adapter 100. The bushing 20 is further described below.

As discussed above, the locking adapter 100 can include a first leg 110 and a second leg 112 connected to first leg 110. As also discussed above, the locking adapter 100 can include a surgical instrument-engagement portion which can secure to one or more portions of the surgical instrument 12. Such a surgical instrument-engagement portion can include the first coupling portion 120 (discussed above) and/or a second coupling portion 130. The second coupling portion 130 can be connected with an end of the second leg 112. For example, the second coupling portion 130 can be connected to the second (free) end of the second leg 112. In some embodiments, the second coupling portion 130 is integral with the second leg 112. In some embodiments, the second coupling portion 130 extends from the second leg 112 in a direction that is non-parallel to a length of the second leg 112. For example, the second leg 112 can have a length extending between a first (connected) end and a second (free) end thereof, and the second coupling portion 130 can extend from the second leg 112 (and/or the second end of the second leg 112) at an angle that is equal to 10 degrees, 20 degrees, 30 degrees, 40 degrees, 50 degrees, 60 degrees, 70 degrees, 80 degrees, 90 degrees, 100 degrees, 110 degrees, 120 degrees, 130 degrees, 140 degrees, 150 degrees, 160 degrees, or 170 degrees with respect to the length of the second 112, or any value therebetween, or any range bounded by any combination of these values, although other values outside these ranges are possible. In some embodiments, the second coupling portion 130 extends toward an end of the first leg 110 and/or a first coupling portion 120 connected to first leg 110.

In some embodiments, the second coupling portion 130 defines the second (free) end of the second leg 112. For example, the second leg 112 of the locking adapter 100 can have a first end which connects to the first leg 110 and a second (free) end, opposite the first end, which is defined by the second coupling portion 130. The second coupling portion 130 can curl and/or extend in a direction that is non-parallel with respect to a portion of a length of the second leg 112 between the first end (connected to the first leg 110) and the second (free) end of the second leg 112. The first end of the legs 110, 112 can be resiliently connected at an apex or corner of the adapter 100. As illustrated, the legs 110, 112 can be cantilevered from the apex or corner.

The second coupling portion 130 can include one or more openings which are sized and/or shaped to receive a portion of the surgical instrument 12. When a portion of the surgical instrument 12 is positioned and/or secured within such one or more openings of the second coupling portion 130, the second coupling portion 130 can secure the locking adapter 100 to the portion of the surgical instrument 12. Further, when the second coupling portion 130 secures to the portion of the surgical instrument 12 in such manner, another portion of the locking adapter 100 (such as the tool-engagement portion 124*b*) can secure to a portion of a surgical tool 30 so as to attach the surgical tool 30 to the surgical instrument 12. Additionally, as described in more detail below, the second coupling portion 130 can work alongside the first coupling portion 120 to secure the locking adapter 100 to the surgical instrument 12.

As shown in at least FIGS. 2A-2B, the second coupling portion 130 can comprise a foot 132 which can at least partially receive, secure to, and/or engage a portion of the surgical instrument 12. For example, the foot 132 can include an opening 132*a* that can be sized and/or shaped to receive a portion of the surgical instrument 12. For example, the opening 132*a* can be sized and/or shaped to accommodate and/or surround a cross-section (or a portion of a cross-section) of the surgical instrument 12. The opening 132*a* can have a cross-section that is circular, square, rectangular, pentagonal, hexagonal, heptagonal, octagonal, nonagonal, or decagonal, for example. The opening 132*a* can be a hole.

As discussed in further detail below, the locking adapter 100 can be adjusted between different positions by moving the first leg 110 with respect to the second leg 112. The locking adapter 100 can include one or more finger grips which advantageously allow a user to better handle or grip the locking adapter 100 so as to move the first leg 110 with respect to the second leg 112. For example, with reference to FIGS. 2A-2K, the locking adapter 100 can include a first recessed portion 150*a*. The first recessed portion 150*a* can be positioned along a surface of the first leg 110. For example, the first recessed portion 150*a* can be positioned at or near a first (free) end of the first leg 110 and/or can be positioned along an exterior surface of the first leg 110 that faces away from the second leg 112 (and/or that faces away from a direction that the first coupling portion 120 extends from the first leg 110). The first recessed portion 150a can be recessed from a plane or surface of the first leg 110. In some embodiments, the first recessed portion 150a is sized and/or shaped to conform to a shape of a finger of a user. For example, the first recessed portion 150a can be sized and/or shaped to conform to a shape of a thumb or index finger of a user.

Figure 2G:
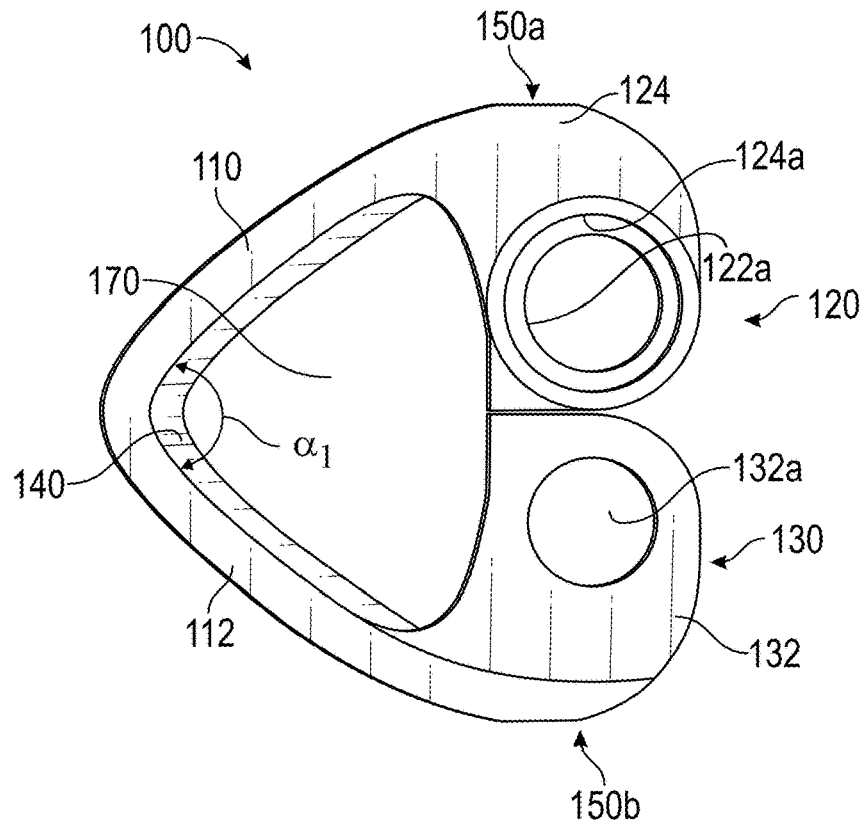
FIG. 2G illustrates a right side view of the locking adapter of FIG. 1A.

The locking adapter 100 can include a second recessed portion 150b. The second recessed portion 150b can be positioned along a surface of the second leg 112. For example, the second recessed portion 150b can be positioned at or near the second (free) end of the second leg 112 and/or can be positioned along an exterior surface of the second leg 112 that faces away from the first leg 110 (and/or that faces away from a direction that the second coupling portion 130 extends from the second leg 112). The second recessed portion 150b can be recessed from a plane or surface of the second leg 112. In some embodiments, the second recessed portion 150b is sized and/or shaped to conform to a shape of a finger of a user. For example, the second recessed portion 150b can be sized and/or shaped to conform to a shape of a thumb or index finger of a user.

Where the locking adapter 100 includes both a first and second recessed portion 150a, 150b, the first and second recessed portions 150a, 150b can align with each other. For example, as shown in FIG. 2G, an axis extending through a center of the first recessed portion 150a can align with an axis extending through a center of the second recessed portion 150b. Such axes may align with arrows $F_1$ and $F_2$ as shown in FIG. 2I, for example. In some embodiments, the first recessed portion 150a aligns vertically with the second recessed portion 150b, where "vertical" represents the up and down direction in the orientation of FIG. 2G.

With reference to FIGS. 2J-2K, either or both of the first or second recessed portions 150a, 150b can have a concave shape with respect to a width of the first and/or second legs 110, 112 of the locking adapter 100. For example, either or both of the first or second recessed portions 150a, 150b can be shaped so that a middle of the recessed portion(s) 150a, 150b is lower than ends of the recessed portion(s) 150a, 150b at edges of the width(s) of the first and/or second legs 110, 112.

As shown in at least FIGS. 2A-2C and 2G-2I, the locking adapter 100 can include a rib 140. The rib 140 can extend from an interior surface of the first leg 110 and/or an interior surface of the second leg 112. The interior surfaces of the first leg 110 and the second leg 112 are opposite the previously-described exterior surfaces of the first leg 110 and the second leg 112. The interior surfaces of the first leg 110 and the second leg 112 face at least partially toward the first and/or second coupling portions 120, 130 and/or at least partially toward each other. The rib 140 can extend outward from one or both interior surfaces of the first and second legs 110, 112 and along a portion of the lengths of the legs 110, 112. The rib 140 can be spaced inwards from exterior edges or widths of the first and second legs 110, 112 (see FIG. 2A). The rib 140 can extend along the first leg 110 between the first coupling portion 120 and the second end of the first leg 110 which connects to the second leg 112. Additionally or alternatively, the rib 140 can extend along the second leg 112 between the second coupling portion 130 and the first end of the second leg 112 which connects to the first leg 110. The rib 140 can provide stiffness to the locking adapter 100 which can advantageously help bias the locking adapter 100 to a neutral position where the first coupling portion 120 is spaced away from the second coupling portion 130 (see FIG. 2G).

As discussed above, the locking adapter 100 can be adjusted between different positions by moving the first leg 110 with respect to the second leg 112. For example, a force $F_1$ can be applied to a portion of the first leg 110 (such as at or near a free end of first leg 110) and a force $F_2$ can be applied to a portion of the second leg (such as at or near a free end of the second leg 112) in order to move the first coupling portion 120 toward the second coupling portion 130. In various embodiments, the legs 110, 112 are resiliently connected, so removal of the forces $F_1$, $F_2$ results in the legs 110, 112 returning to substantially their original positions. In some embodiments, the legs 110, 112 move toward each other when such forces are applied and away from each other when force is released. In certain implementations, the legs 110, 112 are configured to be pinched toward each other. The locking adapter 100 can have a first position (neutral/open position) where the first and second coupling portions 120, 130 are spaced apart from each other (see FIG. 2A). In such first position, the one or more openings (for example, the openings 122a and/or 124b and 132a) of the first and second coupling portions 120, 130 can be not aligned with one another. For example, in the first position, the axes extending through the openings 122a and/or 124a and 132a can be not aligned with each other. In such first position, the axes extending through the openings 122a and/or 124a and 132a can be not aligned with each other but can be parallel to each other.

The locking adapter 100 can have a second position (flexed/closed position) where the first and second coupling portions 120, 130 are adjacent and/or proximate each other. For example, as shown in FIG. 2I, in the second position, the first and second coupling portions 120, 130 can be positioned side-by-side. In such second position, the one or more openings (for example, the openings 122a and/or 124a and 132a) of the first and second coupling portions 120, 130 can be aligned with one another. For example, in the second position, axes extending through the openings 122a and/or 124a and 132a can be aligned with each other. In the second position, the surgical instrument 12 can be passed through the opening 122a, opening 124a, and/or opening 132a.

As discussed above, in some embodiments, the first coupling portion 120 can include more than one foot, for example, a first foot 122 and a second foot 124, and such feet 122, 124 can be spaced apart from one another by a gap. For example, as shown in FIG. 2J, the first foot 122 can be spaced from the second foot 124 by gap $G_1$. $G_1$ can be equal to or greater than a width of the second coupling portion 130 (and/or the foot 132). As also discussed, the first foot 122 can include an opening 122a and the second foot 124 can include an opening 124a. In such configurations, when the locking adapter 100 is in the second position (the position as shown in FIG. 2I), the foot 132 (or a portion of foot 132) of the second coupling portion 130 can be positioned within the gap $G_1$ and between the first and second feet 122, 124 of the first coupling portion 120 and the opening 132a of the foot 132 can be aligned with the opening 122a of the foot 122 and/or the opening 124a of the foot 124 of the first coupling portion 120. As discussed further with reference to FIG. 5 below, when the opening 132a aligns with one or both of the openings 122a, 124a, the surgical instrument 12 can be positioned within and secured by the feet 132, 122, and/or 124.

The locking adapter 100 can have a notch 160. In some embodiments, the notch 160 comprises a window, such as a through-hole. The notch 160 can be configured to facilitate bending of the legs 110, 112 relative to each other. In some implementations, the notch 160 comprises a recess, such as a groove that does not pass entirely through the legs 110, 112. As shown, the notch 160 can be positioned at the intersection of the legs 110, 112 and/or at a corner of the locking adapter 100, such as a corner opposite the openings 122a, 124a.

As shown in at least FIG. 2G, the first leg 110, second leg 112, first coupling portion 120, and second coupling portion 130 can define an opening 170 positioned therebetween and/or extending through an interior of the locking adapter 100. The opening 170 can be triangle-shaped and/or rounded, for example, among other shapes. The opening 170 can be larger when the locking adapter 100 is in the first, open position (as shown in FIG. 2G) than when in the second, closed position (as shown in FIG. 2I). When the locking adapter 100 is in the first and/or second positions described herein, the locking adapter 100 can have a triangular shape. For example, with reference to FIGS. 2G-2H, from a side view, the locking adapter 100 can have a generally triangular peripheral shape.

Bushing

Figure 3A:
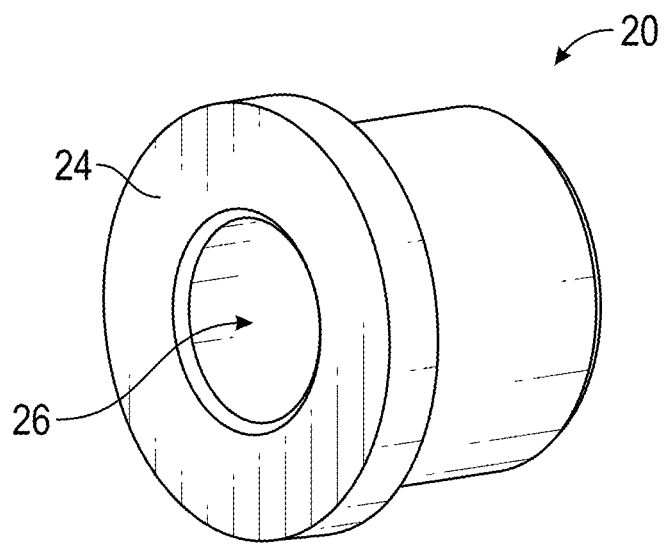
FIGS. 3A-3B illustrate perspective views of the bushing of FIG. 1A.
Figure 3B:
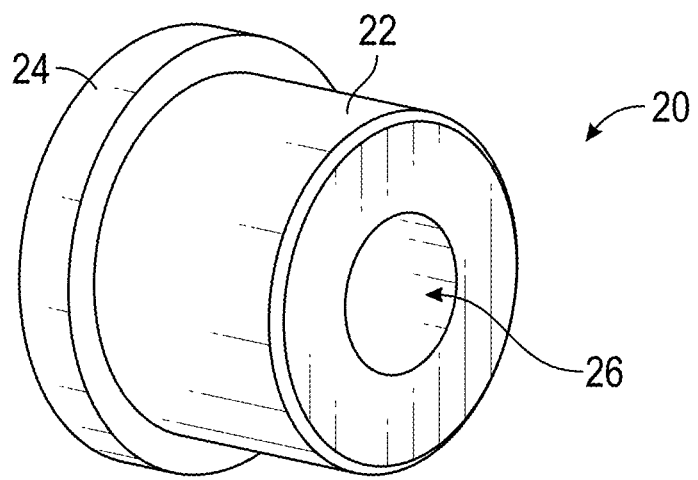

As shown by FIGS. 3A-3B, the bushing can include a first portion configured to receive and/or secure to a portion of the surgical tool 30 and a second portion that is configured to secure to the tool-engagement portion 124b. For example, the bushing 20 can include a through-hole 26 that is sized and/or shaped to receive and/or secure to an end of the surgical tool 30. The through-hole 26 can extend through a length of a body 22 of the bushing 20. The body 22 can be sized and/or shaped to fit within the hollow interior of the tool-engagement portion 124b. For example, where the hollow interior of the tool-engagement portion 124b has a cross-section that is circular, square, rectangular, pentagonal, hexagonal, heptagonal, octagonal, nonagonal, or decagonal, the body 22 of the bushing 20 can have a shape that is cylindrical, square, rectangular, pentagonal, hexagonal, heptagonal, octagonal, nonagonal, or decagonal in order to match the cross-section of the hollow interior of the tool-engagement portion 124b. Additionally, the through-hole 26 can have a cross-section that is sized and/or shaped to receive a portion of the surgical tool 30 (such as an end of the surgical tool 30). For example, the through-hole 26 can have a cross-section that is circular, square, rectangular, pentagonal, hexagonal, heptagonal, octagonal, nonagonal, or decagonal. For example, the cross-sectional area of the through-hole 26 can be greater than a cross-sectional area of the portion of the surgical tool 30 that is positioned and/or secured within the through-hole 26. In some embodiments, a cross-sectional area of the through-hole 26 is equal to a cross-sectional area of the opening 122a of the first foot 122 of the first coupling portion 120.

When the bushing 20 is secured within the hollow interior of the tool-engagement portion 124b, the through-hole 26 can be aligned with the opening 124a and/or the opening 122a. For example, when the bushing 20 is secured within the hollow interior of the tool-engagement portion 124b, an axis extending through a center of the through-hole 26 can align with an axis extending through a center of the opening 124a and/or an axis extending through a center of the opening 122a.

The bushing 20 can include a first end configured to face away from the first coupling portion 110 when secured to the tool-engagement portion 124b and a second end opposite the first end. The first end of the bushing 20 can include a rim 24 which can protrude from and extend along a portion of a cross-section of the body 22. For example, the rim 24 can protrude from and extend along the entire perimeter of the cross-section of body 22 or less than the entire perimeter. When the bushing 20 is positioned and/or secured within the tool-engagement portion 124b, the rim 24 can contact a surface of a free end of the tool-engagement portion 124b so as to prevent the body 22 of the bushing 20 from moving further through the hollow interior of the tool-engagement portion 124b. The rim 24 can protrude from the cross-section of the body 22 a distance smaller than, equal to, or greater than a thickness of the tool-engagement portion 124b. The bushing 20 can be secured to and/or within the tool-engagement portion 124b by a press-fit, snap-fit, friction-fit, or another configuration.

Surgical Tool

Figure 4A:
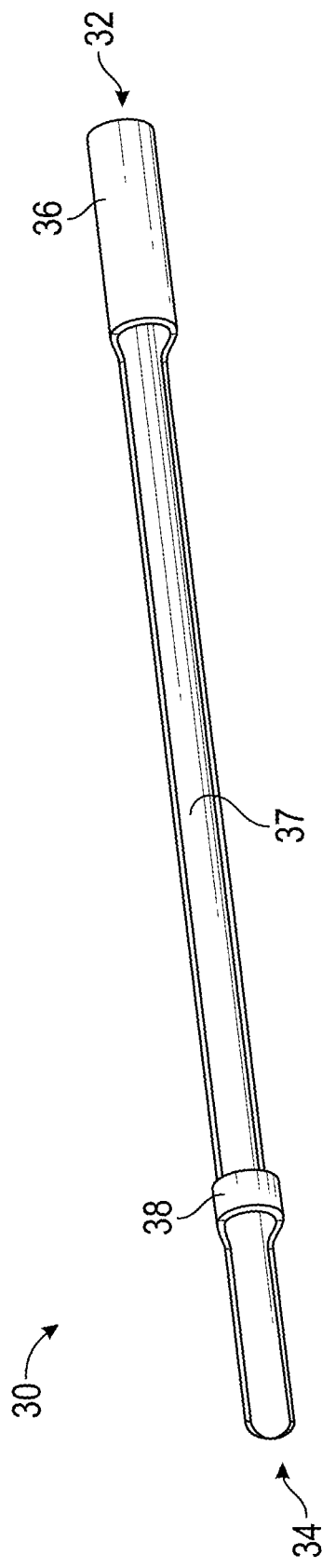
FIGS. 4A-4C illustrate perspective views of the tool of FIG. 1A.
Figure 4B:
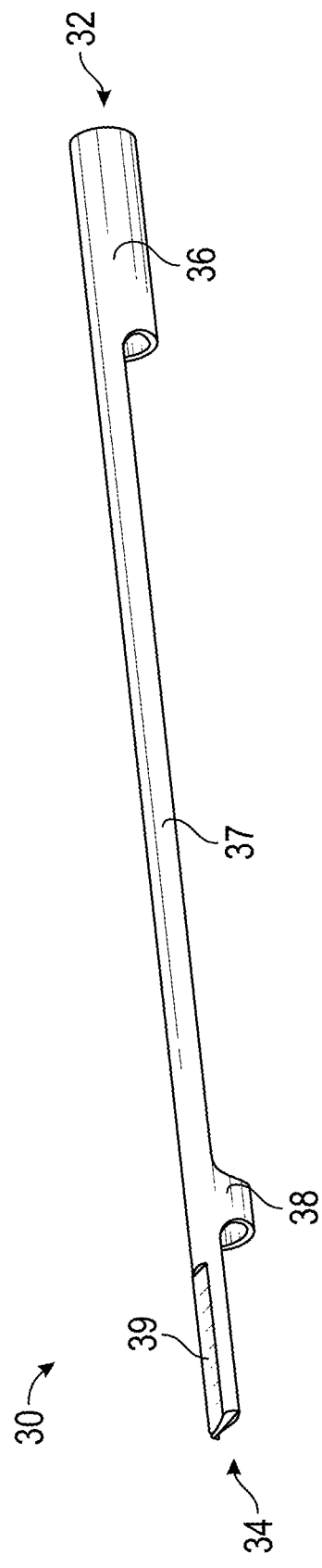
Figure 4C:
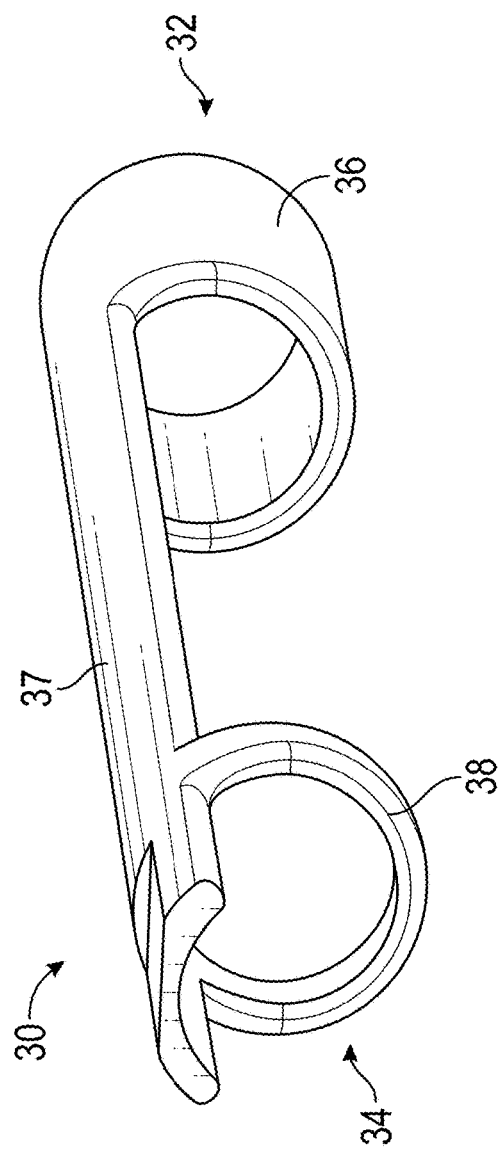

FIGS. 4A-4C illustrate various views of a surgical tool 30. The surgical tool 30 can include a first end 32, a second end 34 opposite the first end 32, and a length extending between the first and second ends 32, 34. As discussed above, the surgical tool 30 can be configured to at least partially secure to and/or around the surgical instrument 12. For example, the surgical tool 30 can include a shaft 37 extending along the length of the surgical tool 30 between the first and second ends 32, 34 and one or more collars sized and/or shaped to receive, surround, and/or partially secure to portions of the surgical instrument 12. For example, as shown, the surgical tool 30 can include a first collar 36 positioned proximate to or at first end 32 of tool 30. The first collar 36 can be sized and/or shaped to fit and/or secure within the tool-engagement portion 124b of the locking adapter 100 and/or the through-hole 26 of the bushing 20 where the cross-section of the hollow interior of the tool-engagement portion 124b is larger than the cross-section of the collar 36 such that the bushing 20 fills the gap therebetween. The first collar 36 can have a shape that is cylindrical, square, rectangular, pentagonal, hexagonal, heptagonal, octagonal, nonagonal, or decagonal in order to match the cross-section of the hollow interior of the tool-engagement portion 124b or the through-hole 26 of the bushing 20. The first collar 36 can have a hollow interior sized and/or shaped to match a cross-section of the surgical instrument 12 so that a portion of the surgical instrument 12 can fit within the collar 36.

The surgical tool 30 can additionally include a second collar 38. The second collar 38 can be sized and/or shaped to receive and/or surround a portion of the surgical instrument 12. The second collar 38 can have a shape that is cylindrical, square, rectangular, pentagonal, hexagonal, heptagonal, octagonal, nonagonal, or decagonal. In some embodiments, the second collar 38 has a length that is smaller than a length of the first collar 36. However, the length of the second collar 38 can be equal to or greater than the length of the first collar 36. The second collar 38 can be positioned along the length of the shaft 37 at different positions. For example, the second collar 38 can be positioned along the shaft 37 and spaced apart from the end 34 to which the first collar 36 is positioned. The second collar 38 can be longitudinally spaced apart from the first collar 36.

The first and second collars 36, 38 can at least partially support and/or secure the surgical tool 30 to the surgical instrument 12. For example, when the surgical instrument 12 is positioned within the first and/or second collars 36, 38, the surgical instrument 12 can be inhibited or prevented from moving relative to the surgical tool 30 in a direction that is perpendicular (e.g., vertical) with respect to an axis that extends through the surgical instrument 12.

In some embodiments, a reflective surface is positioned on or integral with a portion of the surgical tool 30. For example, as shown in FIG. 4B, the reflective surface 39 can be positioned on or integral with the surgical tool 30 proximate or at the end 34 of the surgical tool 30. The reflective surface 39 can be flat or curved (for example, concave or convex). The reflective surface 39 can be recessed from a surface of the shaft 37 (for example, an exterior surface of the shaft 37 that faces away from the collars 36, 38). In some embodiments, other types of tools can be positioned on or be integral with a portion of the surgical tool 30. For example, a temperature sensor, physiological sensor (e.g., optical sensor), electrodes (e.g., for measuring properties of nearby tissue), one or more cameras, a cauterizer, a marker (e.g., for marking a tissue near a surgical site), among other tools can be positioned on or integral with a portion of the surgical tool 30. Such exemplary sensors can couple via electrical wiring to the handpiece 10 or can connect to a power source independent of the handpiece 10.

As shown in FIGS. 4A-4C, the shaft 37 can have a small thickness or cross-section so as to minimize the weight and/or material of the tool 30, which can advantageously provide better maneuverability of the tool 30. The shaft 37 can have a partially circular cross-section. For example, the shaft 37 can have a cross-section that is c-shaped. The cross-section of the shaft 37 can be rounded.

Example Methods of Attachment of the Surgical Tool

Figure 5:
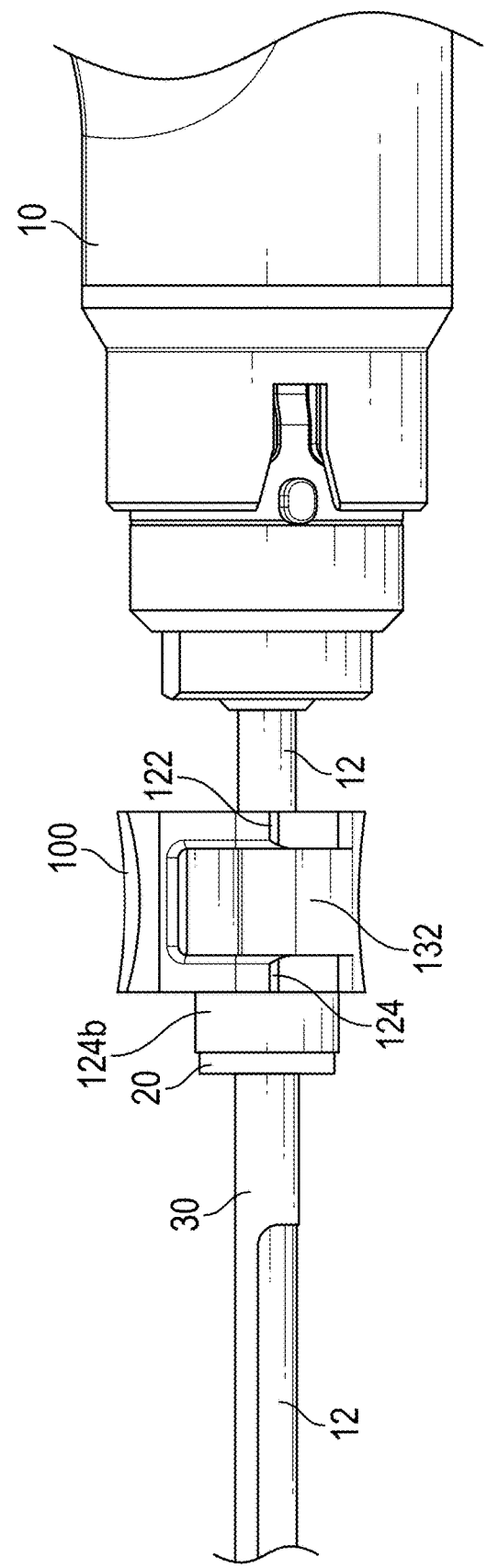
FIG. 5 illustrates an enlarged side view of a portion of FIG. 1A in accordance with aspects of this disclosure.

FIG. 5 illustrates an enlarged view of a portion of the assembly shown in FIG. 1A. As discussed above, the locking adapter 100 can advantageously secure a surgical tool 30 to a surgical instrument 12 at a point of use in a surgical environment. Such securement can be achieved in a variety of ways.

Figure 2H:
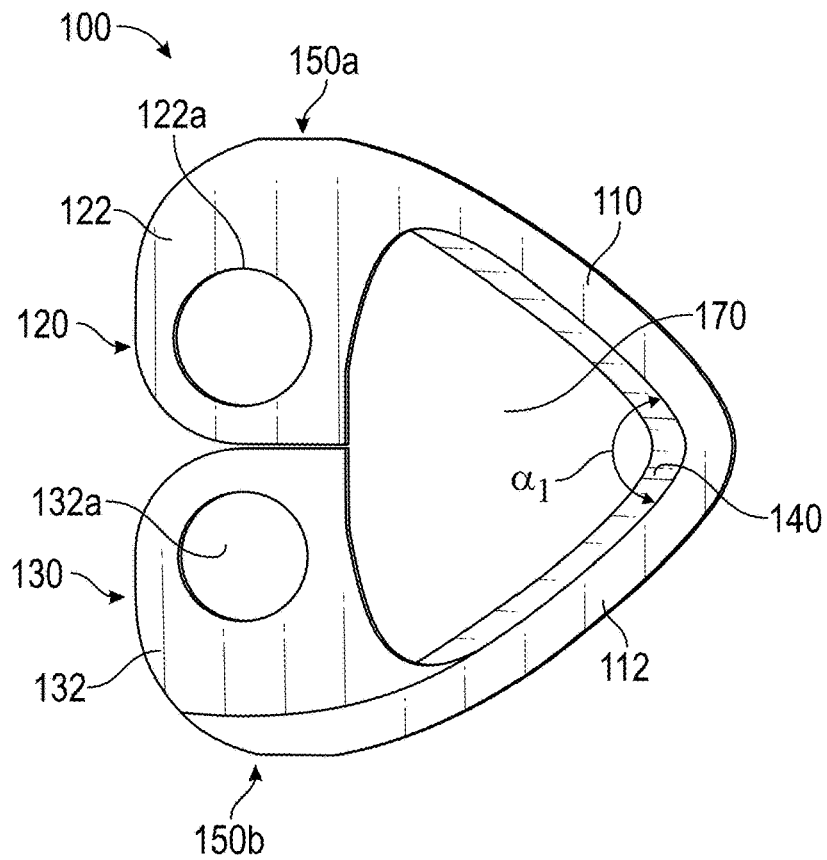
FIG. 2H illustrates a left side view of the locking adapter of FIG. 1A.
Figure 2I:
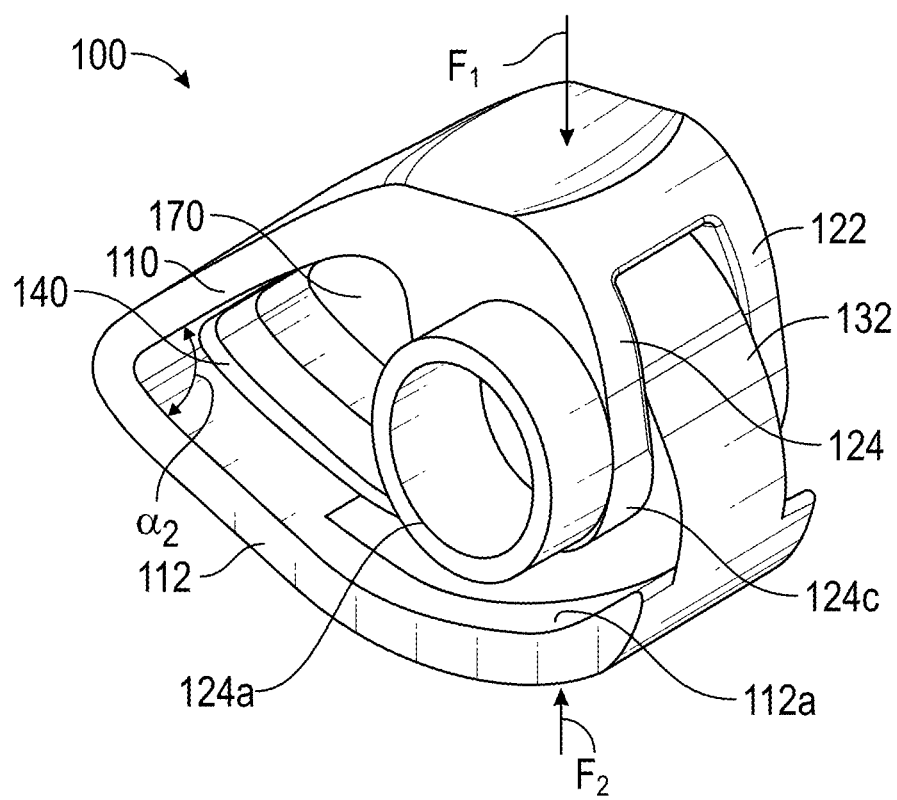
FIG. 2I illustrates another perspective view of the locking adapter of FIG. 1A, where the locking adapter is shown in a closed position in accordance with aspects of this disclosure.

For example, with reference to FIGS. 2G-2I and 1B, forces (such as $F_1$ and $F_2$) can be applied to the locking adapter 100 so as to move the first coupling portion 120 towards the second coupling portion 130 so that the locking adapter 100 moves from the first position to the second position. At the first position (FIGS. 2G-2H), an angle at an apex or corner of an intersection of the leg 110 and the leg 120 can be $\alpha_1$. At the second position (FIG. 2I), an angle at an apex or corner of an intersection of the leg 110 and the leg 120 can be $\alpha_2$. As shown in FIGS. 2G-2I, the angle $\alpha_1$ between the legs 110 and 120 when the locking adapter 100 is in the first position can be greater than the angle $\alpha_2$ between the legs 110 and 120 when the locking adapter 100 is in the second position. In the second position, as discussed previously, one or more openings of the first and second coupling portions 120, 130 (such as the openings 132a and the opening 122a and/or 124a) can align with one another. This can enable the surgical instrument 12 to be longitudinally inserted through such openings. After the surgical instrument 12 is inserted through such openings, the locking adapter 100 can be "released" (for example, a user stops gripping or applying forces $F_1$ and $F_2$ to the locking adapter 100). Because of the structure and configuration of the locking adapter 100 and its natural bias toward the first position (where the one or more openings of the first and second coupling portions 120, 130 are not aligned), the locking adapter 100 will attempt to pull apart (e.g., the first and second coupling portions 120, 130 will attempt to move away from each other and/or in different directions). Such attempt of the first and second coupling portions 120, 130 to pull apart can be inhibited or prevented by the physical interference of the surgical instrument 12 within the openings of the first and second coupling portions 120, 130. This in turn results in forces being applied onto portions of the surgical instrument 12 by the first and second coupling portions 120, 130.

In some variants, the first and second coupling portions 120, 130 can pinch the surgical instrument 12 when the locking adapter 100 is released. For example, where the first coupling portion 120 includes the first and second feet 122, 124 having openings 122a, 124a and the surgical instrument 12 is positioned within such openings 122a, 124a, the first and second feet 122 apply forces on the surgical instrument 12 in a direction towards the free end of the first leg 110 (for example, upwards in the orientation of FIG. 5) and/or in a direction generally perpendicular to the longitudinal axis of the instrument 12. At the same time, when the surgical instrument 12 is positioned within the opening 132a of the foot 132 of the second coupling portion 130, the foot 132 applies a force on the surgical instrument 12 that is equal and opposite to the forces that the first and second feet 122, 124 apply. The forces applied by the feet 122, 124, 132 onto the surgical instrument 12 can act to secure the locking adapter 100 to the surgical instrument 12. In some variants, the locking adapter 100 is automatically secured to the surgical instrument 12 when forces (such as those described above) are released.

In some embodiments, the first and second legs 110, 112 can cooperate to restrict or limit rotation and/or movement with respect to one another. For example, as shown in FIG. 2I, one or more portions 112a of an interior surface of the second leg 112 can interfere with a portion 124c of the first coupling portion 120 (e.g., the foot 124) so as to limit the rotation and/or movement of the first coupling portion 120 and/or the first leg 110 with respect to one or both of the second leg 112 and/or the second coupling portion 130 when the locking adapter 100 moves from the first position (FIGS. 2G-2H) to the second position (FIG. 2I). In some embodiments, the portion 124c is a surface (e.g., bottom surface) of the first coupling portion 120 (e.g., a first and/or second foot 122, 124 of the first coupling portion 120) which faces the portion 112a of the interior surface of the second leg 112 (see FIG. 2I).

Before, after, or during (e.g., simultaneously) the securement of the locking adapter 100 to the surgical instrument 12 in the manner described above, the surgical tool 30 can be at least partially secured to the surgical instrument 12 by positioning the surgical instrument 12 through the one or more collars (e.g., the collars 36, 38) of the surgical tool 30. Before, after, or during such sliding, the end 32 of the surgical tool 30 can be secured to the locking adapter 100 by directly securing the end 32 and/or the collar 36 to the tool-engagement portion 124b or by indirectly securing the end 32 and/or the collar 36 to the tool-engagement portion 124b using the bushing 20. As discussed above, the bushing 20 can include the through-hole 26 which can secure to the end 32 of the surgical tool 30. Before, after, or during the securement (direct or indirect) of the end 32 of the surgical tool 30 to the tool-engagement portion 124b, the bushing 20 can be secured to the locking adapter 100 by positioning the body 22 within the hollow interior of the tool-engagement portion 124b as discussed above. The surgical instrument 12 can be attached to the handpiece 10 before, after, or during any of the above-described steps. In certain embodiments, the tool 30 connects directly to the adapter 100 without the bushing 20. For example, in some variants, an end of the tool 30 is connected directly to the wall surrounding the opening 124a.

Thus, regardless of the precise order in which the tool 30, surgical instrument 12, bushing 20, locking adapter 100, and/or handpiece 10 are assembled, the assembly provides a convenient method by which a surgical tool 30 can be attached to a surgical instrument 12.

Certain Terminology

Conditional language used herein, such as, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. The term "and/or" means that "and" applies to some embodiments and "or" applies to some embodiments. Thus, A, B, and/or C is equivalent to A, B, and C written in one sentence and A, B, or C written in another sentence. The term "and/or" is used to avoid unnecessary redundancy.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees.

Some embodiments have been described in connection with the accompanying drawings. The figures are drawn to scale, but such scale should not be limiting, since dimensions and proportions other than what are shown are contemplated and are within the scope of this disclosure. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

SUMMARY

This disclosure has presented certain embodiments, examples, and variations of the surgical tool attachment devices, systems, and methods. However, this disclosure extends beyond the specifically disclosed embodiments, examples, and variations to other alternative embodiments and/or uses of the invention, as well as obvious modifications and equivalents thereof. In addition, while a number of variations have been shown and described in detail, other modifications, which are within the scope of this disclosure, will be readily apparent to those of skill in the art based upon this disclosure. Moreover, while certain examples have been discussed in the context of attachments for surgical tools, the various inventions disclosed herein are not limited to use in surgical tools. Indeed, the various inventions disclosed herein are contemplated for in use a variety of other types of medical devices and other medical environments.

Certain features have been described in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Any portion of any of the steps, processes, structures, and/or devices disclosed or illustrated in one embodiment, flowchart, or example in this disclosure can be combined or used with (or instead of) any other portion of any of the steps, processes, structures, and/or devices disclosed or illustrated in a different embodiment, flowchart, or example. The embodiments and examples described herein are not intended to be discrete and separate from each other. Combinations, variations, and other implementations of the disclosed features are within the scope of this disclosure.

Any of the steps and blocks can be adjusted or modified. Other or additional steps can be used. None of the steps or blocks described herein is essential or indispensable. Moreover, while operations may be depicted in the drawings or described in the specification in a particular order, such operations need not be performed in the particular order shown or in sequential order, and that all operations need not be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products.

The various features and processes described above may be used independently of one another, or may be combined in various ways. All possible combinations and subcombinations are intended to fall within the scope of this disclosure. In addition, certain method, event, state, or process blocks may be omitted in some implementations. The methods and processes described herein are also not limited to any particular sequence, and the blocks or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

In summary, various embodiments and examples of the surgical tool attachment devices, systems, and methods have been disclosed. Although the disclosure has been in the context of those embodiments and examples, this disclosure extends beyond the specifically disclosed embodiments to other alternative embodiments and/or other uses of the embodiments, as well as to certain modifications and equivalents thereof. Moreover, this disclosure expressly contemplates that various features and aspects of the disclosed embodiments can be combined with, or substituted for, one another. Accordingly, the scope of this disclosure should not be limited by the particular disclosed embodiments described above, but should be determined only by a fair reading of the claims that follow.

The following is claimed:

1. An adapter for removably securing a tool to a surgical instrument, the adapter comprising:
a first leg having a first end and a second end;
a second leg having a first end and a second end, wherein the first end of the second leg connects with the first end of the first leg to form a curved joint;
a first coupling portion at the second end of the first leg and comprising a first opening; and
a second coupling portion at the second end of the second leg and comprising a second opening;
wherein:
the adapter has a first position in which the first opening of the first coupling portion is misaligned with the second opening of the second coupling portion;
the adapter has a second position in which the first opening of the first coupling portion is at least partially aligned with the second opening of the second coupling portion;
when the adapter is in the second position and a portion of the surgical instrument is received by the first and second openings, the first and second coupling portions apply a gripping force to the portion of the surgical instrument;
when the adapter is in the first position, a first axis extending through a center of the first opening is generally parallel to a second axis extending through a center of the second opening; and
said first and second legs pivot about said curved joint when the adapter is transitioned from the first position to the second position.

2. The adapter of claim 1, wherein:
when the adapter is in the first position, the first and second legs are angled relative to one another at a first angle;
when the adapter is in the second position, the first and second legs are angled relative to one another at a second angle; and
the second angle is less than the first angle.

3. The adapter of claim 1, wherein each of the first and second openings comprises a circular hole.

4. The adapter of claim 1, wherein, when the adapter is in the second position, the first axis extending through the center of the first opening is parallel to the second axis extending through the center of the second opening.

5. The adapter of claim 1, wherein:
the first coupling portion comprises at least one foot extending outward from the second end of the first leg, the at least one foot comprising the first opening; and
the second coupling portion comprises at least one foot extending outward from the second end of the second leg, the at least one foot of the second coupling portion comprising the second opening.

6. The adapter of claim 5, wherein:
the at least one foot of the first coupling portion comprises a first foot and a second foot, the first foot comprising the first opening and the second foot comprising a third opening;
the third opening is at least partially aligned with the first and second openings when the adapter is in the second position; and
when the adapter is in the second position and the portion of the surgical instrument is received by the first, second, and third openings, the first and second coupling portions apply the gripping force to the portion of the surgical instrument.

7. The adapter of claim 6, wherein the first foot and the second foot are spaced apart from one another by a gap that is sized to accommodate the at least one foot of the second coupling portion such that the at least one foot of the second coupling portion is positioned between the first foot and the second foot when the adapter is in the second position.

8. The adapter of claim 1, further comprising a tool-engagement portion for engaging an end of the tool.

9. The adapter of claim 8, wherein the tool-engagement portion extends outward from the first coupling portion adjacent the first opening.

10. The adapter of claim 8, wherein the tool-engagement portion extends outward from the first coupling portion around an entire perimeter of the first opening.

11. An adapter for removably securing a tool to a surgical instrument, the adapter comprising:
a pair of legs connected and resiliently movable relative to one another about a curved joining region;
a first coupling portion on a portion of one of the pair of legs, the first coupling portion comprising a first opening; and
a second coupling portion on a portion of the other one of the pair of legs, the second coupling portion comprising a second opening;
wherein the adapter has a first position and a second position, and wherein:
when the adapter is in the first position, the first and second openings are misaligned with one another;
when the adapter is in the second position, the first and second openings are at least partially aligned with one another such that a portion of the surgical instrument can be inserted through the first and second openings;
the adapter is biased towards the first position;
when the adapter is in the first and second positions, a first axis extending through a center of the first opening is generally parallel to a second axis extending through a center of the second opening; and
the first and second legs pivot about said curved joining region when the adapter is transitioned from the first position to the second position.

12. The adapter of claim 11, wherein:
when the adapter is in the first position, the pair of legs are angled relative to one another at a first angle; and when the adapter is in the second position, the pair of legs are angled relative to one another at a second angle that is less than the first angle.

13. The adapter of claim 11, further comprising a tool-engagement portion extending outward from the first coupling portion and configured for engaging an end of the tool.

14. An adapter for removably securing a tool to a surgical instrument, the adapter comprising:
a first leg comprising a first receiving region, the first receiving region comprising a first opening;
a second leg comprising a second receiving region, the second receiving region comprising a second opening;
a biased apex integral with and connecting the first and second legs such that the first and second legs are resiliently movable relative to each other;
the adapter configured such that:
in response to a force being applied against a bias of the apex to the first and second legs, the adapter transitions from a first state in which the first and second openings are misaligned to a second state in which the first and second openings are at least partially aligned, thereby permitting a portion of the surgical instrument to be inserted through the first and second openings; and
in response to the force being removed from the first and second legs, the adapter applies a gripping force to the portion of the surgical instrument, thereby securely coupling the adapter to the surgical instrument;
wherein, when the adapter is transitioned from the first state to the second state, at least one of the first and second legs pivots about a first axis that is generally parallel to a second axis that extends through a center of the first or second opening.

15. The adapter of claim 14, wherein:
when the adapter is in the first state, the first and second legs are angled relative to one another at a first angle; and
when the adapter is in the second state, the first and second legs are angled relative to one another at a second angle that is less than the first angle.

16. The adapter of claim 14, further comprising a tool-engagement portion adjacent the first receiving region of the first leg and configured for engaging an end of the tool.

17. The adapter of claim 16, wherein the tool-engagement portion extends around an entire perimeter of the first opening.

18. An adapter for removably securing a tool to a surgical instrument, the adapter comprising:
a first leg having a first end and a second end;
a second leg having a first end and a second end, wherein the first end of the second leg connects with the first end of the first leg to form a curved joint;
a first coupling portion at the second end of the first leg and comprising a first opening; and
a second coupling portion at the second end of the second leg and comprising a second opening;
wherein:
the adapter has a first position in which the first opening of the first coupling portion is misaligned with the second opening of the second coupling portion;
the adapter has a second position in which the first opening of the first coupling portion is at least partially aligned with the second opening of the second coupling portion;
when the adapter is in the second position and a portion of the surgical instrument is received by the first and second openings, the first and second coupling portions apply a gripping force to the portion of the surgical instrument;
when the adapter is transitioned from the first position to the second position, at least one of the first and second legs pivots about a first axis that is generally parallel to a second axis that extends through a center of the first or second opening;
said first and second legs pivot about said curved joint when the adapter is transitioned from the first position to the second position.

* * * * *